US007772182B2

(12) United States Patent
Liu et al.

(10) Patent No.: US 7,772,182 B2
(45) Date of Patent: Aug. 10, 2010

(54) STABLE SUSPENSION FORMULATIONS OF ERYTHROPOIETIN RECEPTOR AGONISTS

(75) Inventors: Kui Liu, Redwood City, CA (US); Michael A. Desjardin, Sunnyvale, CA (US); Beth L. Hill, Sunnyvale, CA (US); Zengji Li, San Ramon, CA (US)

(73) Assignee: Alza Corporation, Mountain View, CA (US)

( * ) Notice: Subject to any disclaimer, the term of this patent is extended or adjusted under 35 U.S.C. 154(b) by 241 days.

(21) Appl. No.: 11/194,850

(22) Filed: Aug. 1, 2005

(65) Prior Publication Data
US 2006/0030526 A1 Feb. 9, 2006

Related U.S. Application Data

(60) Provisional application No. 60/599,564, filed on Aug. 5, 2004.

(51) Int. Cl.
*A61K 38/18* (2006.01)
(52) U.S. Cl. ......................................... 514/8
(58) Field of Classification Search ...................... None
See application file for complete search history.

(56) References Cited

U.S. PATENT DOCUMENTS

| 3,109,774 | A | 11/1963 | White |
| 3,111,458 | A | 11/1963 | White |
| 4,732,889 | A | 3/1988 | Cynshi |
| 4,745,099 | A | 5/1988 | Akamatsu |
| 4,992,419 | A | 2/1991 | Woog |
| 5,376,632 | A | 12/1994 | Konings |
| 5,597,562 | A | 1/1997 | Nomura |
| 5,643,575 | A | 7/1997 | Martinez |
| 5,674,534 | A | 10/1997 | Zale et al. |
| 5,688,679 | A | 11/1997 | Powell |
| 5,716,644 | A | 2/1998 | Zale et al. |
| 5,730,969 | A | 3/1998 | Hora |
| 5,904,935 | A | 5/1999 | Eckenhoff et al. |
| 6,020,004 | A | 2/2000 | Shah |
| 6,245,740 | B1 | 6/2001 | Goldenberg et al. |
| 6,264,990 | B1 | 7/2001 | Knepp et al. |
| 6,333,306 | B1 | 12/2001 | Lehmann |
| 6,440,932 | B1 | 8/2002 | Lehmann |
| 6,503,534 | B1 | 1/2003 | Pellet |

(Continued)

FOREIGN PATENT DOCUMENTS

EP 503583 9/1992

(Continued)

OTHER PUBLICATIONS

Van Anh Tran Nguyen et al. Erythropoietic recovery during treatment with Darbepoietin-alpha after impaired rHuEPO response to anemia in two patients with osteomyelofibrosis after peripheral blood stem cell transplantation. Hematology Journal, vol. 4, Issue 6, pp. 456-458 (2003).*

(Continued)

*Primary Examiner*—Marianne P Allen
*Assistant Examiner*—Regina M DeBerry

(57) ABSTRACT

A suspension formulation for therapeutic use includes a non-aqueous, single-phase vehicle exhibiting viscous fluid characteristics and a particle formulation comprising an erythropoietin receptor agonist dispersed in the vehicle.

10 Claims, 3 Drawing Sheets

U.S. PATENT DOCUMENTS

| | | |
|---|---|---|
| 6,610,317 B2 | 8/2003 | Straub |
| 6,645,528 B1 | 11/2003 | Straub |
| 6,875,432 B2 | 4/2005 | Liu et al. |
| 7,097,827 B2 * | 8/2006 | Platz et al. .................. 424/45 |
| 2001/0038859 A1 | 11/2001 | Maskiewicz et al. |
| 2002/0009789 A1 | 1/2002 | Hanyu |
| 2002/0037841 A1 | 3/2002 | Papadimitriou |
| 2002/0049161 A1 | 4/2002 | Lehmann |
| 2002/0058624 A1 | 5/2002 | Hanyu |
| 2002/0098203 A1 | 7/2002 | Gustavsson |
| 2002/0142050 A1 | 10/2002 | Straub |
| 2002/0160956 A1 | 10/2002 | Lehmann |
| 2003/0035845 A1 | 2/2003 | Zale |
| 2003/0041602 A1 | 3/2003 | Williams |
| 2003/0108609 A1 | 6/2003 | Berry |
| 2003/0148938 A1 | 8/2003 | Sharma et al. |
| 2003/0185888 A1 * | 10/2003 | Wong et al. .................. 424/473 |
| 2003/0211167 A1 | 11/2003 | Gustavsson |
| 2004/0087507 A1 | 5/2004 | Yamazaki et al. |
| 2005/0008661 A1 * | 1/2005 | Fereira et al. ................ 424/400 |
| 2005/0112188 A1 * | 5/2005 | Eliaz et al. .................. 424/450 |
| 2005/0250704 A1 | 11/2005 | Bassarab et al. |
| 2006/0029551 A1 | 2/2006 | Liu et al. |

FOREIGN PATENT DOCUMENTS

| | | |
|---|---|---|
| EP | 614666 | 9/1994 |
| WO | WO 93/25221 | 12/1993 |
| WO | WO 96/40073 | 12/1996 |
| WO | WO 00/27419 | 5/2000 |
| WO | WO 01/07075 | 2/2001 |
| WO | WO 01/93837 | 12/2001 |
| WO | WO 2004/056338 | 7/2004 |

OTHER PUBLICATIONS

Online Medical Dictionary. Published at the Centre for Cancer Education, University of Newcastle upon Tyne The CanceWEB project (Copyright 1997-2005) http://cancerweb.ncl.ac.uk/cgi-bin/omd?query=saccharose.

* cited by examiner

STABLE SUSPENSION FORMULATIONS OF ERYTHROPOIETIN RECEPTOR AGONISTS

CROSS-REFERENCE TO RELATED APPLICATIONS

This application claims priority from U.S. provisional application No. 60/599,564, filed Aug. 5, 2004, the content of which is incorporated herein by reference.

BACKGROUND OF INVENTION

The invention relates generally to pharmaceutical formulations formulated for continuous delivery.

Erythropoietin (EPO) is a pleiotropic glycoprotein hormone produced primarily by the kidney. EPO stimulates the bone marrow to produce red blood cells and exerts tissue protective effects, e.g., neuroprotection, outside the bone marrow. EPO exerts its biological effect by binding to its cell surface receptor. EPO receptor agonists (ERAs) are a class of recombinant molecules that can activate EPO receptors. The recombinant molecules in the ERA class may or may not contain sequence homology to native human EPO (hEPO). Examples of products in the ERA class containing sequence homology to native hEPO are shown in Table 1 below.

TABLE 1

| Product Name | Recombinant Molecule | Homology of Amino Acid sequence to human erythropoietin |
|---|---|---|
| PROCRIT ®/EPOGEN ® | Epoetin alfa | 100% |
| EPREX ®/ERYPO ® | Epoetin alfa | 100% |
| NeoRecormon ® | Epoetin beta | 100% |
| ARANESP ® | Darbepoetin alfa | 97% |

ERA products have been indicated for treatment of anemia due to chronic renal failure, anemia associated with cancer chemotherapy and surgery, and anemia secondary to AZT treatment of AIDS. ERA products currently on the market are administered to patients by subcutaneous or intramuscular injection thrice a week (EPREX®, ERYPO®, and PROCRIT®) or once a week (ARANESP®). Several ERA products currently on the market are liquid, are required to be stored at 2 to 8° C., and are unstable at room and elevated temperatures. ERAs are susceptible to aggregation, which can lead to reduced potency of the drug and may induce unwanted side effects. Adverse side effects associated with current administration of ERAs include, but are not limited to, thrombotic events, infection, hypertension, myalgia, and headache.

The therapeutic effects associated with administration of ERAs may be increased if ERAs could be delivered continuously in a low dose using, for example, implantable delivery devices such as osmotic, mechanical, or electromechanical pump implants. Use of implantable delivery devices generally assures patient compliance since implantable devices are not easily tampered with by the patient and can be designed to provide therapeutic doses of drug over period of weeks, months, or even years without patient input. With one insertion of the device, rather than injections every few days, there is reduced site irritation, fewer occupational hazards for patients and practitioners, reduced waste disposal hazards, improved cost effectiveness through decreased costs of equipment for repeated injections, and increased efficacy when compared to injections that require multiple administrations over relatively short time intervals.

In order to deliver ERAs from an implantable delivery device at a controlled rate over a prolonged period, ERAs must be contained within formulations that maintain their stability at elevated temperature, e.g., 37° C. or higher, over the operational life of the device, and the formulation must be in flowable form.

SUMMARY OF INVENTION

In one aspect, the invention relates to a suspension formulation comprising a non-aqueous, single-phase vehicle exhibiting viscous fluid characteristics and a particle formulation comprising an erythropoietin receptor agonist dispersed in the vehicle.

In another aspect, the invention relates to a method of stimulating erythropoiesis in a subject which comprises administering to the subject an effective amount of a suspension formulation as described above.

In yet another aspect, the invention relates to an implantable delivery device which comprises a reservoir containing a suspension formulation as described above in an amount sufficient to provide continuous delivery of an erythropoietin receptor agonist at a therapeutically effective rate in an environment of use.

Other features and advantages of the invention will be apparent from the following description.

DETAILED DESCRIPTION OF PREFERRED EMBODIMENTS

Figure 1:
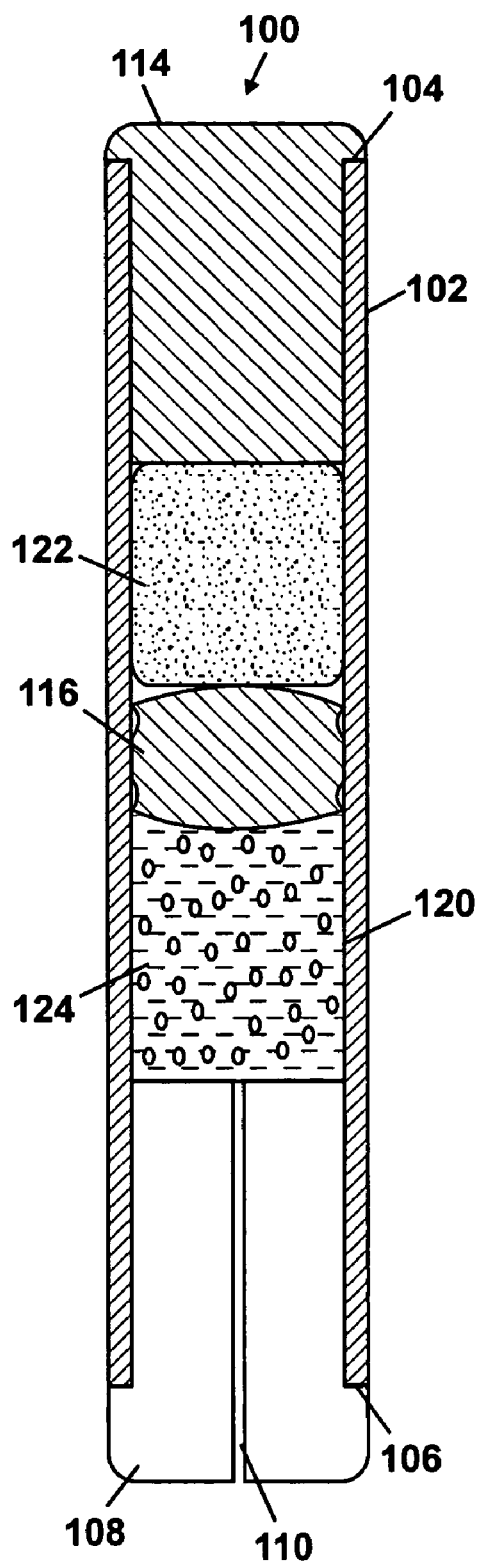
FIG. 1 is a schematic of an osmotic pump containing an ERA formulation according to one embodiment of the invention.
Figure 2A:
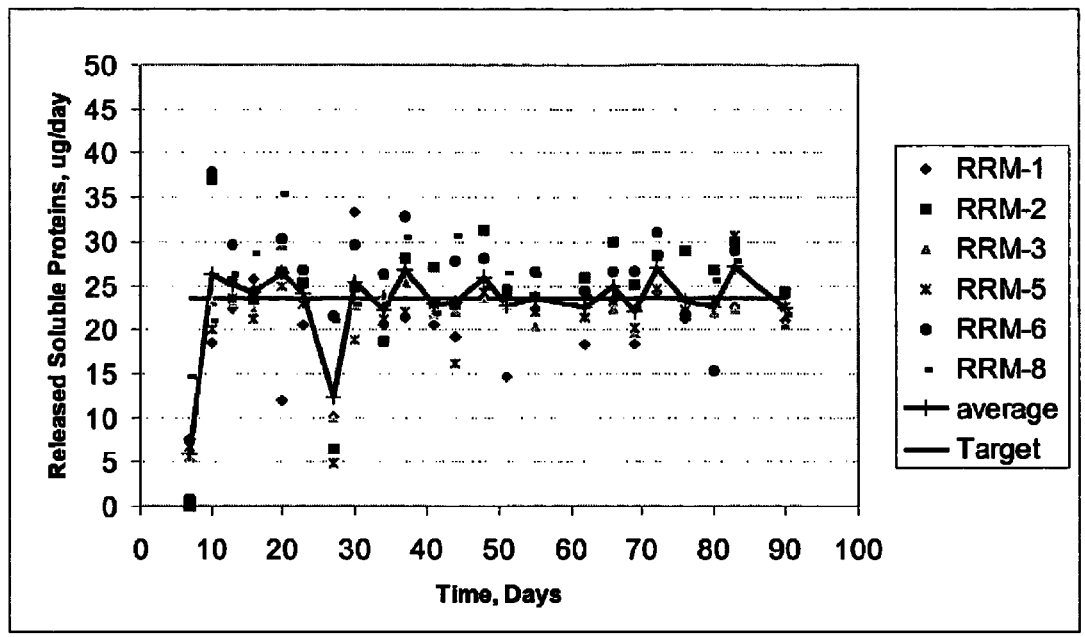
FIG. 2A shows release rate for osmotic pumps containing an ERA formulation according to one embodiment of the invention, wherein the osmotic pumps are pumping into release rate medium.
Figure 2B:
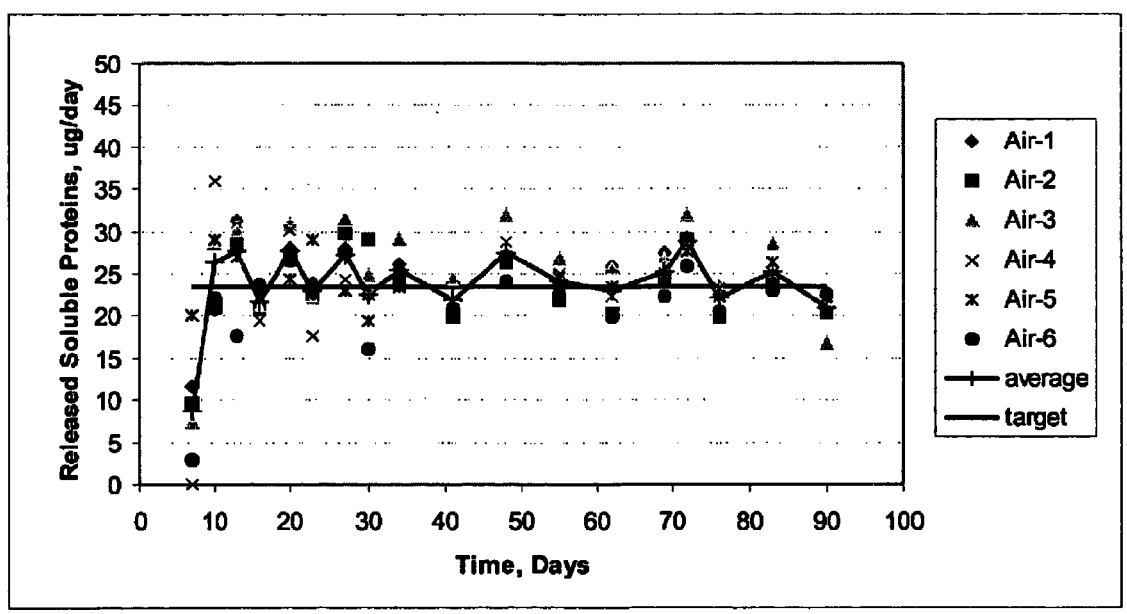
FIG. 2B shows release rate for osmotic pumps containing an ERA formulation according to one embodiment of the invention, wherein the osmotic pumps are pumping into air.
Figure 3:
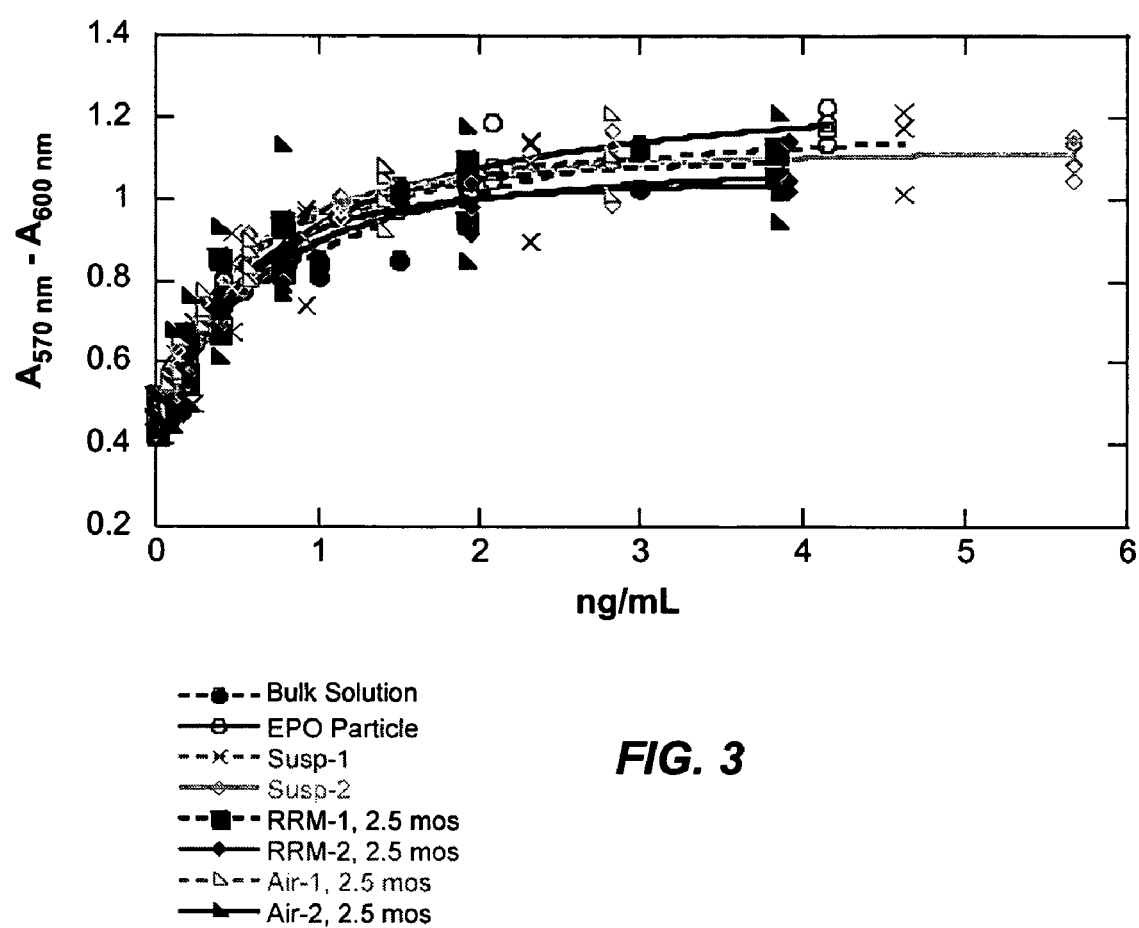
FIG. 3 shows bioactivity of released formulation according to one embodiment of the invention.

The invention will now be described in detail with reference to a few preferred embodiments. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the accompanying drawings and the following discussion.

Embodiments of the invention provide stable formulations of erythropoietin receptor agonists (ERAs) that are deliverable at a controlled rate over a sustained period using, for example, an implantable delivery device. The invention is based in part on the discovery that suspending an ERA particle formulation in a non-aqueous, single-phase vehicle yields a suspension formulation of ERA that is stable at elevated temperature, e.g., 37° C. or higher, for a long duration, e.g., 3 months to 12 months. The ERA particle formulation generally has a low moisture content, preferably less than 5%, prior to being suspended in the vehicle. The ERA particle formulation may be formed using techniques known in the art for forming protein particles, such as spray-drying and lyophilization. The ERA particle formulation may be entirely pure ERA or may be pure ERA formulated with one or more adjuvants or excipients.

The term "ERA" or "erythropoietin receptor agonist" refers to a class of molecules that can activate EPO receptors. These molecules may or may not contain sequence homology to native hEPO. An ERA according to one embodiment of the invention may be selected from the group consisting of polypeptides and proteins having the biological activity of recombinant hEPO, EPO analogs, EPO isoforms, EPO mimetics, EPO fragments, hybrid EPO proteins, fusion protein oligomers and multimers of the above, homologues of the above, glycosylation pattern variants of the above, muteins of the above, and EPO molecules containing the minor modifications enumerated above. ERAs according to the present invention shall not be limited by method of synthesis or manufacture and shall include those synthesized or manufactured by recombinant (whether produced from cDNA or genomic DNA), synthetic, transgenic, and gene activated methods.

Particularly preferred ERAs are those that are capable of stimulating erythropoiesis in a mammal. Examples of ERAs capable of stimulating erythropoiesis in a mammal include, but are not limited to, epoetin alfa (trade name EPREX®, ERYPO®, PROCRIT®), epoetin beta (trade name NEO-RECORMON®), and darbepoetin alfa (trade name NESP™, ARANESP®). One form of darbepoetin alfa is described in PCT Publication WO 95/05465 (Amgen, Inc.), the tutorial content of which is incorporated herein by reference. In the WO 95/05465 publication, a darbepoetin alfa includes an analog of hEPO comprising an amino acid sequence which includes at least one additional site or a rearrangement of at least one site for glycosylation. The glycosylation site is for an N-linked or O-linked carbohydrate chain.

Other ERAs indicated as capable of stimulating erythropoiesis in a mammal include hEPO analog, such as human serum albumin fusion proteins described in PCT Publication WO 99/66054 (Genzyme Transgenics Corp), the tutorial content of which is incorporated herein by reference, and EPO mutants, such as described in PCT Publication WO 99/38890 (Beth Israel Deaconess Medical Center), the tutorial content of which is incorporated herein by reference. In the WO 99/38890 publication, an EPO mutant includes an isolated nucleic acid encoding EPO, where the nucleic acid has one or more mutations in a non-coding region and the EPO has altered biological activity. In one embodiment, the mutation is in the 51 non-coding region.

Other ERAs indicated as capable of stimulating erythropoiesis in a mammal include EPO omega, which may be produced from an Apa I restriction fragment of the hEPO gene described in U.S. Pat. No. 5,688,679 (Powell), the tutorial content of which is incorporated herein by reference, and altered glycosylated hEPO, such as described in PCT Publication WO 99/11781 (Hoechst Marion Roussel Deutschland GMBH), the content of which is incorporated herein by reference. In the WO 99/11781 publication, the altered glycosylated hEPO includes a polypeptide having part or all of the primary structural conformation of EPO that is a product of eukaryotic expression of an exogenous DNA sequence.

Another ERA identified as capable of stimulating erythropoiesis in a mammal includes polyethylene glycol (PEG) conjugated erythropoietin analogs described in, for example, PCT Publications WO 98/05363 (Ortho Pharmaceutical Corporation), the tutorial content of which is incorporated herein by reference, and WO 01/76640 (Amgen, Inc.), the tutorial content of which is incorporated herein by reference, and U.S. Pat. No. 5,643,575 (Martinez et al.), the content of which is incorporated herein by reference.

Other examples include cell lines modified for expression of endogenous human EPO as described in PCT Publication WO 99/05268 (Boehringer Mannheim GMBH), the tutorial content of which is incorporated herein by reference, and WO 94/12650 (Transkaryotic Therapies, Inc.), the tutorial content of which is incorporated herein by reference. Tissue and cyto-protective forms of ERAs are also contemplated.

ERAs according to the invention may also include long-acting forms of EPO. As used herein, a "long-acting EPO" includes sustained release compositions and formulations of EPO with increased circulating half-life, typically achieved through modification, such as reducing immunogenicity and clearance rate, and EPO encapsulated in polymer microspheres.

One example of a long-acting EPO is disclosed in PCT publication WO 02/49673 (F. Hoffman-La Roche AG), the content of which is incorporated herein by reference. The WO 02/49673 publication describes a conjugate comprising an erythropoietin glycoprotein having an N-terminal alpha-amino group, chosen from hEPO or its analogs having sequence of hEPO modified by addition of 1-6 glycosylation sites or a rearrangement of a glycosylation site, where the glycoprotein is covalently linked to a PEG group.

Other examples of long-acting EPO include, but are not limited to, PEG-modified EPO disclosed in PCT publication WO 02/32957 (Chugal Seiyaku Kabushiki Kaisha, Japan), conjugates of glycoproteins having erythropoietic activity and having at least one oxidized carbohydrate moiety covalently linked to a non-antigenic polymer disclosed in PCT publication WO 94/28024 (Enzon, Inc.), and other PEG-EPO prepared using succinimidyl carboxymethylated PEG (SCM-PEG), succinimidyl propionate PEG (SPA-PEG), and SBA-PEG.

In one embodiment of the invention, ERA is stabilized against aggregation at elevated temperature, e.g., 37° C. or higher, prior to being suspended in the non-aqueous, single-phase vehicle. In one embodiment, ERA is stabilized against aggregation with a stabilizer and a buffer. In one embodiment, the stabilizer includes sugar. The sugar may be present in the ERA particle formulation in an amount ranging from 0.1 to 99.9% by weight. Examples of sugars that may be included in the particle formulation include, but are not limited to, sucrose, trehalose, glucose, lactose, maltose, and fructose. In one embodiment, the buffer used in the particle formulation is present in an amount ranging from 0.1 to 99.8% by weight. Preferably, the buffer has a pH value between 5.0 and 8.0, more preferably between 5.5 and 7.5. In one embodiment, the buffer concentration is in a range from 5 mM to 50 mM in solution. Examples of buffers include, but are not limited to, citrate, histidine, phosphate, succinate, maleate, tris, acetate, carbonate, and gly-gly. Of these examples, citrate and histidine buffers are most preferred. The ratio of stabilizer to ERA can be variable. With citrate buffer, the ratio of stabilizer to ERA is preferably greater than 2.0.

In other embodiments of the invention, the stabilizer used in the ERA particle formulation may further include one or more components selected from the group consisting of amino acids, polyols, and polymers. The particle formulation may include 0 to 99.9% by weight amino acid, 0 to 99.9% by weight polyol, and 0 to 99.9% by weight polymer. Examples of amino acids that may be incorporated in the particle formulation include, but are not limited to, histidine, glycine, alanine, L-leucine, glutamic acid, isoleucine, methionine, L-threonine, 2-pheylamine, and arginine. Examples of polyols that may be incorporated in the particle formulation include, but are not limited to, sorbital and mannitol. Examples of polymers that may be incorporated in the particle formulation include, but are not limited to, polyvinylpyrrolidone (PVP), dextran, and propylene glycol.

The particle formulation may include other excipients selected from, for example, surfactants, bulking agents, and salts. The particle formulation may include 0 to 10 wt %, preferably 0 to 5 wt %, of a surfactant, 0 to 99.9 wt %, preferably 0 to 70 wt %, of a bulking agent, and 0 to 99.9 wt %, preferably 0 to 70 wt %, of a salt. The surfactant included in the particle formulation may be ionic or nonionic. Examples of surfactants include, but are not limited to, polyoxyethylene (20) sorbitan monolaurate (trade name TWEEN® 20), polyoxyethylene sorbitan monooloeate (trade name TWEEN® 80), polyoxyethylene-polyoxypropylene glycol (trade name PLURONIC® F68), and sodium docecyl sulfate (SDS). Examples of bulking agents include, but are not limited to, mannitol and glycine. Examples of salts include, but are not limited to, sodium chloride, calcium chloride, and magnesium chloride.

Table 2 below gives examples of lyophilized Epoetin alfa (EPO) compositions stabilized against aggregation, along with their total soluble aggregate as measured by Size Exclusive Chromatography (SEC) when the compositions are stored at 37° C. for 3 months.

react with the ERA. Where the components of the vehicle include polymer and solvent, the vehicle preferably has little or no phase separation of the polymer from the solvent when the vehicle is mixed with water, for example, to reduce the occurrence of partial or complete blockage of the delivery device during drug administration. The components of the vehicle are chosen such that the vehicle has little or no solubility for the selected ERA, thereby maintaining the selected ERA as dry particles, thereby achieving stability of the selected ERA.

In one embodiment, the vehicle includes at least one polymer. The polymer is preferably biocompatible and may be biodegradable or non-biodegradable. Examples of polymers useful in forming the vehicle include, but are not limited to, pyrrolidones such as polyvinylpyrrolidone (having a molecular weight of 2,000 to 1,000,000), poly(lactides), poly(glycolides), poly(lactide-co-glycolide), polylacticpolyglycolic acid (PLGA), poly(lactic acid)s, poly(glycolic acid)s, polyoxy-ethylene-polyoxy-propylene block copolymers (exhibiting a high viscosity at 37° C.), such as PLURONIC® 105, and esters or ethers of unsaturated alcohols such as vinyl acetate. The vehicle may also include any pharmaceutically-acceptable solvent that can be combined with the polymer to yield a vehicle that is non-aqueous, single-phase, biocompatible, and miscible with water. Examples of solvents useful in forming the vehicle include, but are not limited to, benzyl benzoate

TABLE 2

| Formulation | Sucrose:EPO Ratio | EPO loading (wt %) | TWEEN® 20 (wt %) | Citrate, mM in solution before lyophilization | Total soluble aggregate (%) |
|---|---|---|---|---|---|
| A | 2.5 | 17.8 | 1 | 25 | 0.95 |
| B | 2.5 | 18.0 | 0 | 25 | 0.90 |
| C | 13.5 | 6.0 | 1 | 25 | 0.07 |
| D | 13.5 | 6.0 | 0 | 25 | 0.08 |
| E | 2.5 | 25.6 | 0 | 5 | 0.32 |
| F | 13.5 | 6.6 | 1 | 5 | 0.20 |
| G | 8 | 9.7 | 0.5 | 15 | 0.08 |
| H | 13.5 | 6.7 | 0 | 5 | 0.00 |
| I | 2.5 | 24.6 | 1 | 5 | 0.24 |
| J | 4.2 | 16.5 | 0.5 | 10 | 0.18 |

A non-aqueous, single-phase vehicle suitable for use in the invention may be any combination of solvent, polymer (liquid and non-liquid), non-polymer (liquid and non-liquid), and surfactant. The components of the vehicle are chosen such that the vehicle is miscible with water, although it is not necessary that every component of the vehicle is readily miscible with water. The components of the vehicle are selected and combined such that the resulting vehicle is a homogeneous system that is both physically and chemically uniform throughout. The vehicle is biodegradable in that it disintegrates or breaks down over a period of time in response to a biological environment. The breakdown of the vehicle in the biological environment may take place by one or more physical or chemical processes, such as by enzymatic action, oxidation, reduction, hydrolysis (e.g., proteolysis), displacement, or dissolution by solubilization, emulsion or micelle formation.

The components of the vehicle of the invention are selected such that the vehicle has a viscosity in a range from about 1,000 to 10,000,000 poise, preferably 10,000 to 250,000 poise. To maintain stability of the ERA at elevated temperature, e.g., 37° C. or higher, over a period of time, the components of the vehicle are chosen such that the vehicle does not (BB), benzyl alcohol (BA), lauryl lactate (LL), lauryl alcohol (LA), polyethylene glycols, glycofural (GF), vitamin E.

The vehicle may include more than one different polymer or different grades of a single polymer. The vehicle may also include more than one solvent combined with the polymer(s). In particular, two or more solvents may be required to provide a vehicle that is both miscible in water and facilitates production of a stable ERA formulation. The amount of polymer(s) and solvent(s) included in the vehicle may be varied to provide a vehicle having desired performance characteristics. In general, the vehicle would include about 40 to 80 wt % polymer(s) and about 20 to 60 wt % solvent(s).

Beyond polymers and solvents, the vehicle may also include other excipients such as one or more surfactants or preservatives. Surfactants that may be used in the vehicle include, but are not limited to, polysorbates, such as available under the trade name TWEEN®, ethylene-oxide-propylene-oxide copolymers, such as available under the trade name PLURONIC®, fatty acid esters of sorbitan, such as available under the trade name SPAN®, glyceryl caprylate, glyceryl laurate, PEG-8 caprylic capric glycerides, polyglyceryl-6 oleate, dioctyly sodium, sulfosuccinate, and Vitamin E TPGS. The surfactant(s) may be included in the vehicle to facilitate release of ERA from the vehicle once the formulation is delivered to an environment of use or to help maintain the stability of ERA when ERA is suspended in the vehicle. Where included, the surfactant(s) will typically account for less than 20 wt %, preferably less than 10 wt %, more preferably less than 5 wt % of the vehicle. Preservatives that may be used in the vehicle include, for example, antioxidants and antimicrobial agents. Examples of potentially useful antioxidants include, but are not limited to, tocopherol (vitamin E), ascorbic acid, ascorbyl palmitate, butylated hydroxyanisole, butylated hydroxytoulene, and propyl gallate. Where one or more preservatives are incorporated in the vehicle, the amount used will vary depending on the application, the preservative used, and the desired result. Generally, a preservative is included only in amounts sufficient to achieve the desired preservative effect.

However, the vehicle is not limited to those including polymer(s) and solvent(s). As a further example, the vehicle may be one including a non-polymer. Examples of non-polymeric materials include hydrophobic saccharide materials, organogels, or lipid materials that behave as single-phase vehicles. Exemplary saccharide materials include, but are not limited to, sucrose esters that exist as fluids at ambient or physiological temperature, such as sucrose acetate isobutyrate (SAIB). SAIB is a liquid non-polymer. Some non-polymeric materials like SAIB can be used "neat," i.e., without addition of other solvents. The vehicle including a non-polymeric material may also include one or more solvents. The vehicle including a non-polymeric material may also include one or more surfactants, some examples of which are given above. The vehicle including a non-polymeric material may also include preservatives, some examples of which are also given above.

The non-aqueous, single-phase vehicle may be loaded with varying amounts of an ERA particle formulation to provide a suspension formulation that allows dosing of the ERA at a desired rate over a chosen period of time. The suspension formulation may include 0.1 to 40 wt %, preferably 0.1 to 20 wt %, of an ERA. The suspension formulation may be formulated for dispensing from an implantable delivery device at a desired flow rate. The suspension formulation may be formulated to deliver ERA in a range from 1 ng/day to 600 μg/day over a few months to one year. Where ERA is delivered from an osmotic pump implant designed to provide low flow rates, the suspension formulation is preferably formulated for delivery between 0.5 and 5 μL/day, with flow rates of about 1.5 μL/day and 1.0 μL/day being particularly preferred. It should be noted that the suspension formulation is not limited to implantable delivery devices such as pump implants, but may also be used as a depot injection.

The invention also includes an implantable delivery device loaded with an ERA suspension formulation according to embodiments of the invention. The implantable delivery device may be embodied by any delivery system device capable of delivering a flowable formulation at a controlled rate over a sustained period of time after implantation within a subject. An implantable delivery device according to the invention may include, for example, an osmotic pump implant, such as available under the trade name DUROS®, or a regulator-type pump implant, such as available from, for example, Codman of Raynham, Mass., Medtronic of Minneapolis, Minn., and Tricumed Medinzintechnik GmbH of Germany, or other non-osmotic pump implant.

A study was conducted to assess the stability of a particle formulation of EPO (epoetin alfa) in a non-aqueous, single-phase vehicle. The stability of the particle formulation was evaluated using Size Exclusive Chromatography (SEC). The stability was evaluated in terms of EPO loading and total soluble aggregate. EPO loading is the percent of total soluble EPO in the particle formulation including monomer, dimer, and other higher molecular weight products. EPO loading provides some information about whether there are significant amounts of insoluble EPO formed during storage or delivery. The total soluble aggregate is the percentage of the EPO-related compounds that are larger than monomer and soluble in water.

The following examples are presented for illustrative purposes and are not intended to limit the invention as otherwise described herein.

Example 1

An EPO particle formulation was prepared as follows: a bulk solution of EPO was obtained as a frozen solution having a concentration of approximately 3.1 mg/ml. The EPO solution was dialyzed against 10 mM histidine buffer solution. Sucrose (stabilizer) and TWEEN® 20 (surfactant) were added into the dialyzed EPO solution to make EPO to sucrose to surfactant in a desired ratio. The buffered solution was spray-dried into solid particles having EPO:sucrose:Tween 20:10 mM histidine ratio equal to 1:4.53:0.03:0.50, pH of 6.9, and EPO loading of 16.5%.

Example 2

The stability of the EPO particle formulation when stored at elevated temperature was evaluated. Three samples of the EPO particle formulation as prepared in Example 1 were stored at 40° C. for 3 months. The samples were analyzed at initial, 1 month, 2 months, and 3 months using SEC. At initial time point, the EPO particle formulation had an average particle size of approximately 4.5 μm, a glass transition temperature of 54.9±5.6° C., and a moisture content of 1.16±0.01%. Table 3 below shows the stability results. The results show that the EPO particles are stabilized against aggregation when stored at 40° C. for 3 months.

TABLE 3

| | EPO loading (%) | Monomer (%) | Dimer (%) | Total soluble aggregate (%) |
|---|---|---|---|---|
| Initial | 15.8 | 100.0 | 0.00 | 0.00 |
| | 16.0 | 100.0 | 0.04 | 0.04 |
| | 16.0 | 100.0 | 0.00 | 0.00 |
| 1 month at 40° C. | 15.6 | 99.9 | 0.091 | 0.09 |
| | 15.7 | 99.9 | 0.081 | 0.08 |
| | 16.0 | 99.9 | 0.079 | 0.08 |
| 2 months at 40° C. | 15.8 | 99.9 | 0.13 | 0.13 |
| | 16.0 | 99.9 | 0.13 | 0.13 |
| | 15.9 | 99.9 | 0.13 | 0.13 |
| 3 months at 40° C. | 14.9 | 99.8 | 0.16 | 0.16 |
| | 15.2 | 99.9 | 0.13 | 0.13 |
| | 15.6 | 99.8 | 0.15 | 0.15 |

Example 3

A suspension formulation was prepared as follows: EPO particle formulation prepared as described in Example 1 was suspended in Ceraphyl® 31/PVP vehicle with a target particle loading of approximately 10% (w/w).

Example 4

Three samples of the suspension prepared in Example 3 were stored at 40° C. for 3 months in glass containers. The samples were analyzed at initial, 1 month, 2 months, and 3 months using SEC. Table 4 below shows the stability results. A total soluble aggregate of approximately 1.57% was observed for the suspension at 3 months, compared to 0.1% for the EPO powder at 3 months. The results show that EPO suspended in Ceraphyl® 31/PVP vehicle is stable when stored at 40° C. for 3 months.

TABLE 4

|  | EPO loading (%) | Monomer (%) | Dimer (%) | Total soluble aggregate (%) |
|---|---|---|---|---|
| Initial | 1.55 | 99.9 | 0.08 | 0.08 |
|  | 1.58 | 99.9 | 0.09 | 0.09 |
|  | 1.58 | 99.9 | 0.08 | 0.08 |
| 1 month at 40° C. | 1.53 | 99.4 | 0.46 | 0.63 |
|  | 1.53 | 99.5 | 0.40 | 0.48 |
|  | 1.54 | 99.5 | 0.41 | 0.49 |
| 2 months at 40° C. | 1.57 | 98.7 | 1.02 | 1.34 |
|  | 1.57 | 98.8 | 1.05 | 1.22 |
|  | 1.57 | 98.6 | 1.20 | 1.43 |
| 3 months at 40° C. | 1.48 | 98.3 | 1.42 | 1.70 |
|  | 1.48 | 98.3 | 1.04 | 1.67 |
|  | 1.47 | 98.7 | 1.02 | 1.35 |

A study was conducted to assess the release rate of EPO particle formulation suspended in a non-aqueous, single-phase vehicle using an implantable delivery device, such as an osmotic pump implant. FIG. 1 shows a schematic of an osmotic pump implant 100 used in the study. The osmotic pump implant 100 includes a cylinder 102, made of titanium, having open ends 104, 106. A diffusion moderator 108 is mounted at the end 106 of the cylinder 102. The diffusion moderator 108 has a delivery conduit 110 which allows fluid delivery from the interior to the exterior of the cylinder 102. The delivery conduit 110 provided by the diffusion moderator 108 is straight. However, diffusion moderators with configurations other than straight are anticipated and included in the invention. In the study, diffusion moderators with straight delivery conduits having a diameter of 0.25 mm and 0.5 mm and a length of 1.5 mm were used. A semipermeable membrane 114 is inserted at the end 104 of the cylinder 102, forming a fluid-permeable barrier between the exterior and interior of the cylinder 102. A piston 116 and osmotic agent 122 are disposed in the cylinder 102. A drug reservoir 120 is defined inside the cylinder 102.

The following examples are presented for illustrative purposes and are not intended to limit the invention as otherwise described herein.

Example 5

Approximately 150 μL (about 150 mg) of the suspension prepared in Example 3 was loaded into a drug reservoir 120 of an osmotic pump implant 100, as shown at 124 (FIG. 1). The target dose was 3000 IU/day (24 μg/day).

Example 6

Several osmotic pumps were prepared as described in Example 5. The membrane end of each the osmotic pump was placed into a stoppered Vacutainer® filled with 3 mL phosphate buffer saline (PBS), and the diffusion moderator end of the osmotic pump was placed into a dry Vacutainer®. The systems were placed into capped test tubes, with the diffusion moderator side down, and partially immersed in a 37° C. water bath. After 7 days, some of the systems were removed from the water bath and the dry Vacutainers® at the diffusion moderator ends of the systems were replaced with Vacutainers® filled with 2.5 mL release rate medium (20 mM citrate and 50 mg/mL sucrose at pH of 6.9) and the systems were returned to the water bath. Thus, some of the systems pumped into release rate medium (pumping into release rate medium) while others pumped into an empty container (pumping into air).

At specified time points, for the systems pumping into release rate medium, the Vacutainers® at the diffusion moderator ends were replaced with new Vacutainers® filled with 2.5 mL release rate medium as explained above. The samples collected from the Vacutainers® removed from the diffusion moderator ends were analyzed using High Performance Liquid Chromatogram (HPLC). At specified time points, for the systems pumping into air, the systems were removed from the water bath, the Vacutainers® at the diffusion moderator ends were replaced with new dry Vacutainers®, and the systems were returned into the water bath. The samples collected from the Vacutainers® removed from the diffusion moderator ends were weighed and then analyzed using HPLC. The formulation released was collected over 3 or 4 days in order to accumulate enough material for analysis.

The release rate per day over 3 months at 37° C. is plotted in FIGS. 2A and 2B. FIG. 2A shows release rate for the systems pumping into release rate medium. FIG. 2B shows release rate for the systems pumping into air. The results indicate that the systems deliver EPO at a constant and approximately to a target rate (23.5 μg) over 3 months at 37° C. (zero-order delivery). The bioactivity of the released samples were evaluated using a cell proliferation method at the 2.5 month time point. The result is shown in FIG. 3. The result shows that there was no significant reduction of bioactivity for released EPO at 37° C. over 2.5 months compared to the bulk solution. The released EPO contained greater than 99% monomer at 37° C. over 2.5 months.

While the invention has been described with respect to a limited number of embodiments, those skilled in the art, having benefit of this disclosure, will appreciate that other embodiments can be devised which do not depart from the scope of the invention as disclosed herein. The following summarizes exemplary embodiments of the invention.

What is claimed is:

1. A suspension formulation for therapeutic use, comprising:

a non-aqueous, single-phase vehicle exhibiting viscous fluid characteristics and having a viscosity in a range from approximately 1,000 to 10,000,000 poise; and a particle formulation comprising an erythropoietin receptor agonist selected from the group consisting of epoetin alfa, epoetin beta, and darbepoetin alfa dispersed in the vehicle in an amount ranging from approximately 0.1 to 40 wt %, said particle formulation further comprising a stabilizer and a buffer, said stabilizer comprising a sugar and said buffer being selected from the group consisting of histidine and citrate buffers, wherein a ratio of the stabilizer to the erythropoietin receptor agonist is greater than 2.0 when the buffer is a citrate buffer;

wherein the suspension formulation is flowable and stable at 40° C. for at least 3 months.

2. The suspension formulation of claim 1, which is stable at 40° C. for up to 12 months.

3. The suspension formulation of claim 1, wherein the particle formulation has a moisture content less than 5 wt % prior to being dispersed in the vehicle.

4. The suspension formulation of claim 1, wherein the stabilizer further includes one selected from the group consisting of amino acid, polyol, and polymer.

5. The suspension formulation of claim 4, wherein the sugar is sucrose.

6. The suspension formulation of claim 4, wherein the particle formulation further comprises at least one of a surfactant, a bulking agent, and a salt.

7. The suspension formulation of claim 1, wherein the vehicle comprises one or more components selected from the group consisting of solvents, polymers, non-polymers, and surfactants.

8. The suspension formulation of claim 1, wherein the erythropoietin receptor agonist is present in the suspension formulation in an amount ranging from approximately 0.1 to 40 wt %.

9. The suspension formulation of claim 1, which is deliverable using an implantable delivery device.

10. The suspension formulation of claim 1, which produces continuous release of the erythropoietin receptor agonist at target dosage for up to 12 months in an environment of use.

* * * * *